United States Patent [19]

Ecanow

[11] Patent Number: 5,382,437
[45] Date of Patent: Jan. 17, 1995

[54] FROZEN LIQUIFIED GAS COMPOSITION AND METHOD FOR ORAL ADMINISTRATION OF DRUGS, BIOLOGICALS, NUTRIENTS AND FOODSTUFFS

[75] Inventor: Bernard Ecanow, Wilmette, Ill.

[73] Assignee: Hunter Research Corporation, Wilmette, Ill.

[21] Appl. No.: 142,714

[22] Filed: Oct. 25, 1993

[51] Int. Cl.6 .................... A61K 9/20; A61K 9/14
[52] U.S. Cl. ........................... 424/499; 424/464; 424/466; 424/489; 426/384; 426/385
[58] Field of Search ............. 424/464, 466, 489, 499; 426/385, 384

[56] References Cited

U.S. PATENT DOCUMENTS

| | | | |
|---|---|---|---|
| 4,371,516 | 2/1983 | Gregory et al. | 424/485 |
| 4,477,452 | 10/1984 | Haeger | 426/384 |
| 4,616,047 | 10/1986 | Lafon | 426/384 |
| 4,832,956 | 5/1989 | Gergely et al. | 424/480 |
| 4,946,684 | 8/1990 | Blank et al. | 424/441 |
| 5,039,540 | 8/1991 | Ecanow | 426/385 |
| 5,079,018 | 1/1992 | Ecanow | 426/385 |
| 5,206,025 | 4/1993 | Courteille et al. | 424/464 |
| 5,215,756 | 6/1993 | Gole et al. | 424/484 |
| 5,298,261 | 3/1994 | Pebley et al. | 424/464 |

*Primary Examiner*—Thurman K. Page
*Assistant Examiner*—Amy Hulina
*Attorney, Agent, or Firm*—Marshall, O'Toole, Gerstein, Murray & Borun

[57] ABSTRACT

A readily dissolved carrier material having sufficient rigidity for administration of drugs, nutrients, vitamins, biologically-active materials, foodstuffs and combinations thereof capable of rapid dissolution by saliva, bodily fluids or other liquid comprising an interim skeletal structure of an ammoniated gel or foam forming material, preferably a proteinaceous material, such as gelatin, that has been ammoniated, rigidified such as with maltodextrin, in the ammoniated state and deammoniated to leave spaces in place of the frozen ammonia. On dissolution by saliva, bodily fluids or other liquids, the composition becomes a liquid system. While the oral route is preferred, other routes may be used to administer the compositions of this method.

12 Claims, No Drawings

FROZEN LIQUIFIED GAS COMPOSITION AND METHOD FOR ORAL ADMINISTRATION OF DRUGS, BIOLOGICALS, NUTRIENTS AND FOODSTUFFS

FIELD OF THE INVENTION

The present invention is directed to semi rigid or rigid, solid carriers having a high degree of void space for carrying drugs, biologically active materials, foodstuffs, e.g., nutrients, and any other medically useful materials or materials capable of sustaining human or animal life. More particularly, the present invention is directed to solid materials, capable of carrying drugs, nutrients and the like, that are capable of relatively immediate dissolution into liquid form upon contact with animal or human saliva or water for oral ingestion. In other embodiments, the solid carriers of the present invention are dissolvable and/or dispersible in aqueous liquids for liquid administration of drugs, nutrients and the like. In any embodiment, the compositions of the present invention are promptly available for adsorption by mammals and can be prepared in the form of tablets, granules, powders or in liquid form for administration to man and animals. In particular, the methods and compositions of the present invention are directed to a new freeze drying process to deammoniate frozen liquid ammonia in gel and foam materials, particularly proteinaceous substances, thereby leaving porous solid materials capable of absorbing and adsorbing high percentages of drugs, nutrients, and the like, and capable of rapid dissolution in aqueous liquids or in the mouth of man and animals for prompt delivery of active materials to the bloodstream.

BACKGROUND OF THE INVENTION AND PRIOR ART

The method and compositions of the present invention are directed to an alternative method of drying drug and nutrient carriers that produce solid, rigid, but rapidly dissolvable drug and nutrient carriers capable of rapid liberation of the active component to the body in a method that yields new and unexpected results over extant methods of freeze drying.

In accordance with an important feature of the present inventions a composition of (1) ammoniated gel or foamed, non-toxic, edible solid carrier material, such as a proteinaceous material, particularly gelatin or a gelatin derivative, e.g., gelatin, gelatin A, gelatin B, modified fluid gelatin, albumin, and the like; or ammoniated gels formed from materials such as acacia, tragacanth, and/or guar gum, or aqueous foams formed with any anionic, cationic or amphoteric surfactant, either synthetic or natural (biosurfactants) e.g., lecithin; together with (2) a non-toxic, edible, polysaccharide, capable of rigidifying the ammoniated gel or foam substance during deammoniation thereof, for example, dextrin or a dextrin derivative, such as maltodextrin, can be dried in accordance with the present invention to leave a porous skeleton carrier, preferably of a proteinaceous material capable of absorbing and/or adsorbing many times its weight in a drug and/or nutrient and the like.

In accordance with one important embodiment of the present invention, the solid, porous, skeletal carrier is formed by drying the fully ammoniated gel foam material from the gel or foamed state by transfer of solid ammonia from the ammoniated material directly to the gas state and atmosphere at ambient conditions of temperature and pressure.

Reference texts such as Remington's Pharmaceutical Sciences, 15th Edition, 1976, and Lachman et al., *The Theory And Practice Of Industrial Pharmacy*, Lea & Febiger, 1978, describe the process of lyophilization as a method to stabilize water and heat-sensitive drugs.

Patent references which include lyophilization in their respective methods are exemplified by Alexander U.S. Pat. No. 4,537,883; Vendel U.S. Pat. No. 3,496,267 and Saferstein, et al. U.S. Pat. No. 4,752,466. In each of these patents a method involving lyophilizing or freeze drying under vacuum conditions of unstable compositions is disclosed.

Aside from the common use of low temperature, the low temperature drying method of the present invention has very little similarity to the process of lyophilization. The differences of method and product between this invention and the well known lyophilization process will become more apparent hereinafter.

Lyophilization involves the use of mechanical equipment and control of vapor pressure to produce stabilized drugs. In contrast, the method of the present invention includes the use of a liquified gas which is frozen and will rapidly vaporize (sublime) at ambient conditions.

SUMMARY OF THE INVENTION

In brief, the present invention is directed to compositions and methods providing porous solids and semi-solids that disintegrate virtually instantaneously when contacted by water, saliva, and aqueous solutions and dispersions and are particularly useful for the oral delivery and ingestion of drugs, nutrients and the like. As used in this disclosure, the term "drug" is used to mean any composition defined as a drug by the Food, Drug and Cosmetic Act and its amendments. Also, the terms "nutrients", "foods" and "foodstuffs" are used interchangeably and are used to mean any composition in liquid, solid or semi-solid form, without limit, or combinations thereof that are ingested and assimilated by an animal, particularly man, to maintain growth and life. These compositions which may be used singly or in any combination in connection with the disclosed delivery system include vitamins, minerals, essential and non-essential amino acids, cations, anions and also fats, proteins and carbohydrates, without limit, including nutritive derivatives therefrom. For purposes of this specification, powdered, granular or other forms of beverages such as coffee, milk and the like are included as "food" compositions that can be prepared by the method of the present invention.

Finished products of this method may be in the form of tablets, powders, granules or liquid forms. Alternatively, finished products of the present invention in the form of powders or granules may be used to prepare emulsions and suspensions of drug, biologically active, medical or nutrient components.

In accordance with an important feature of the present invention, the methods of the present invention also produce useful freeze dried compositions of foods and drug compositions that are more stable, and more capable of dissolution and dispersion than those produced by other methods.

In accordance with an important feature of the present invention, a composition of a gel or foam material and a rigidfying agent for the gel or foam is intimately contacted with a liquified ammonia solvent and the composition temperature is reduced to about −78° C. (at one atmosphere pressure) or lower, or until the total solution becomes a solid frozen mass. The mass is slowly brought to ambient temperature under vacuum conditions and immediately the solid ammonia sublimes or changes state from the solid frozen state to the gas state. In a matter of minutes, e.g., from one minute to thirty minutes, depending on the quantity of the frozen composition, the ammonia is removed and the product is finished. No water or organic solvent need be used.

In this method the liquified ammoniated composition of a gel or foam material and a rigidifying agent therefor is frozen in a vessel suitable for maintaining temperatures of −78° C. or lower. The container is allowed to come to ambient conditions and the escaping ammonia gas is collected in a second container.

The ammonia gas removal steps may be repeated as often as is required to produce the desired complete removal of the ammonia. The removal of the ammonia provides porous, solid drug, biological and/or nutrient delivery compositions in the form of tablets, granules and powders. If desired, the finished solids can be placed in water to rapidly provide liquid delivery compositions.

Incorporation of a desired dose of the medical or nutritional component(s) in the porous solid carriers of the present invention and, as preferred, the addition of one or more flavoring agents complete the process of the present invention. The finished composition is suitable for oral administration and provides new and unexpected rapid liberation of the active component to the bloodstream of the recipient, particularly for epilingual administration. Since the compositions of the present invention disintegrate instantaneously in the mouth of the user, its contents are promptly available for absorption by the body. The finished products of this invention can be prepared as tablets, granules, powders, or as required as liquid forms such as suspensions and can be administered to man and animals. The methods and compositions of the present invention include methods to prepare freeze dried foodstuffs, and produce drug formulations that have improved stability and dispersibility in liquids.

In accordance with an important feature of the present invention, the compositions of the present invention have several advantages over conventional oral dosage forms: (1) the described formulations overcome objectionable tastes of incorporated nutrients and drugs, (2) as compositions of this invention disintegrate in the mouth or when, as an option, the formulations are prepared and taken in liquid form, such as suspensions, the compositions retain the characteristics of a stable suspension, and (3) the medical and nutrient components of the compositions are quickly available for absorption by the body. Finished products of this invention are ideal for persons who have difficulty ingesting drugs, biologically-active materials and nutrients which are commonly prepared as pills or tablets.

Accordingly, an object of the present invention is to provide a new and improved composition and method of manufacturing the composition comprising a porous, dehydrated solid carrier for drugs, biologically-active materials, nutrients, and the like that dissolves unexpectedly quickly in the mouth of the recipient for unexpectedly fast delivery of an active substance to the bloodstream.

Another object of the present invention is to provide a new and improved method of dehydrating a gel or foam solid material, in gel or foam form, by sublimation of solid ammonia. Upon sublimation of the solid ammonia, the gel or foam substantially retains its gelled or foamed volume, and retains sufficient rigidity for handling and oral ingestion. The resulting material is a solid, skeletal carrier that is exceptionally porous, capable of carrying many times its weight in a liquid active substance and capable of unexpectedly quick dissolution when orally ingested.

Another object of the present invention is to provide a new and improved gelatin-polysaccharide solid carrier, and method of manufacturing the solid carrier, for oral administration of active materials, such as drugs, biologically-active materials, foods, nutrients, vitamins and the like that is unexpectedly porous for receipt of the active material and is unexpectedly readily dissolvable in the mouth with saliva so that the active material is quickly assimilated through the mouth tissue or ingested into the GI tract.

Still another object of the present invention is to provide a new and improved method for producing solid carrier material without involving any water or alcohol contact with drugs or nutrients which are unstable when in contact with water or alcohol. The solid carrier material in an anhydrous liquified ammonia solvent is frozen at −78° C. or below and upon being exposed to ambient temperature and pressure will within minutes permit the frozen solid ammonia to escape to the atmosphere as a gas.

In accordance with another important embodiment of the present invention the ammonia gas can be dissolved in water to form an aqueous ammonia solution from a concentration approaching 0% ammonia, preferably at least about 10% by weight ammonia, to a concentration approaching anhydrous liquid ammonia. The greater the concentration of ammonia in the water the more rapid the transfer of ammonia and water from the frozen solid state to the gas state without going through the liquid state. In this alternative method, the following steps are taken: (1) mix the following ingredients together: about 1 gram of flavored gelatin powder or other gelatin based equivalent, about 2 grams of maltodextrose, about 0.5 grams of gelatin A; about 2 grams of sucrose and the required amount of the drug. After mixing the ingredients, add a ten percent (10%) by weight solution of ammonia in distilled water in an amount that will make a final volume of about 100 ml., (2) stir the product of step (1) at a temperature of, for example, 0° C. until the product becomes a clear solution. Next, (3) fill each compartment of a mold with 1 ml. of the product of step (2). Next, (4) store the product of step (3) for about one hour at a temperature of about −20° C. or less until the molded product (tablet) is frozen solid. Next, (5) remove the tablets from the molds in step (4) and place the tablets on blotting paper and transfer to a vacuum chamber maintained at a temperature of 0° C. or below. Vacuum dry the product of step (5) to sublime the frozen ammonia or frozen aqueous ammonia solution until no odor of ammonia remains and the tablets are dry.

The above and other objects and advantages of the present invention will be better understood in conjunction with the following detailed description.

DETAILED DESCRIPTION OF THE PREFERRED EMBODIMENT

The finished products of the present invention may be tablets, granules, powders or liquids. Tablets weighing about 100 to 150 mgs are preferred and may be of any size appropriate for oral administration. The compositions of this method may also be introduced into the body by other routes of administration. The preferred method comprises the following steps: (1) mix the following ingredients together; about 1 gram of flavored gelatin powder or other gelatin based equivalent, about 2 grams of maltodextrose, about 0.5 gram of gelatin A; about 2 grams of sucrose, optionally for palatability, and the required amount of the drug and as preferred, about 1 gram of other desired dosage of flavoring agents or sweeteners, such as aspartane. The quantities may be adjusted as preferred by the formulator.

After mixing these components, (2) add the mixture to a container of about 100 mls. of anhydrous liquified ammonia, maintained at, for example, about −40° C. Shake gently for approximately 30 minutes or until the solution appears clear.

Then (4) fill each compartment of a suitable mold. Store the product of step (4) at a temperature of about −80° C. or lower for about 30 minutes or until the molded product (tablet) is frozen solid. (5) In completion of step (4) the frozen tablets are removed from the mold and placed in a suitable container which is permitted to slowly come to ambient temperature and pressure. The ammonia gas escapes from the frozen tablets and is collected in an adjacent container and is neutralized. (6) Next, place the tablets resulting from step (5) on blotting paper and transfer to a vacuum chamber. (7) Vacuum dry the product of step (6) until no odor of ammonia remains. It should be understood that sublimation of solid (frozen) anhydrous ammonia occurs at ambient pressure. However, vacuum drying is preferred for faster sublimation and for control of the liberated ammonia gas. The resulting product comprises a porous solid suitable for purposes of oral delivery of drugs, nutrients and the like. The product may be in tablet, powdered or granular form, or reconstituted with water or other solvents for a liquid product. In accordance with another important embodiment of the present invention, the desired dose of the drug component is added by means of a pipette to the surface of each tablet after the product has been dried in step (7).

The preferred procedure to add the drug or nutrient component to the porous solid delivery compositions described above is as follows: the component to be added is dissolved in any appropriate solvent, including organic solvents. The dissolved drug is added dropwise by means of a hypodermic syringe or other similar device to the surface of the delivery composition in that amount that will give the desired dose to each product unit. The porous solid, its spaces now containing the drug or nutrient, then is dried using any conventional drying method to remove all traces of the solvent used in the formulation step. As preferred, the drug or nutrient component can be added to the interim product during earlier stages of preparing the porous solids. As preferred by the formulator, any flavoring agent may be added to the product by placing the agent in solution and adding that quantity of the flavoring agent that is preferred to the surface of the product by means of a hypodermic syringe or other metering device.

To prepare a granular form of the composition, the finished product is processed with a rotating granulator or other similar grinding equipment.

To prepare the powder form of this invention, a fine wire mesh with openings ranging from about 50 to 300 microns is used in place of the blister mold used to form tablets. The steps described to produce the tablet dosage form then are followed to produce the powder delivery form.

The starting materials of this method comprise the following compositions, or combinations thereof, including any pharmaceutically acceptable gel or foam materials prepared from any surfactant, synthetic or biological, particularly proteinaceous materials such as gelatin, including types A and B, fluid gelatin and gelatin derivatives and albumin. Other suitable gel or foam forming compounds of biological or synthetic origin, used singly or in combination, include phospholipids, singly or in combination, particularly lecithin and egg lecithin.

Suitable rigidifying agents for such gels, hydrogels, and foam-forming materials include dextrin and dextrin derivatives, such as maltodextrin; and carbohydrates, including the mono-, di-, oligo- and other poly-saccharides. The monosaccharides include without limitation, dextrose, fructose and galactose and the sugar alcohols mannitol, xylitol and sorbitol; the disaccharides include, without limitation, sucrose, lactose and maltose. Oligosaccharides include polymers of the monosaccharide sugars; polysaccharides include dextrans having molecular weights ranging from about 40,000 to about 90,000. The amount of rigidifying agent is an amount sufficient to rigidify the gel or foam material, generally about 0.1 to 5 times the weight of the gel or foam forming material (dry basis).

The oral delivery compositions of the present invention are useful to administer drugs in each of the following categories: drugs acting on the central nervous system; drugs acting at synaptic and neuroeffector sites; autacoids, cardiovascular drugs, drugs affecting renal function and electrolyte metabolism; drugs effecting uterine motility; antibiotic drugs; anti-fungal drugs; antineoplastic drugs; drugs acting on blood and blood forming organs and hormones. Nutrients that are useful for oral delivery in accordance with the present invention include water-soluble vitamins, such as the B vitamins and vitamin C; water soluble trace elements such as copper, selenium, calcium, chromium, zinc, magnesium and iron; electrolytes without limitation including sodium, potassium, magnesium, calcium, lithium, ammonium, phosphorous, chloride, iodide, bromide, fluoride, acetate, sulfate, carbonate, phosphate, lactate, gluconate and lactobionate; also carbohydrates; amino acids including leucine, isoleucine, lysine, methione, phenylalanine, threonine, tryptophan, valine, alanine, arginine, histidine, proline, serine, tyrosine, glycine, taurine and carnitine, as the L-, D- and racemic forms but particularly the L-acids and branched chain amino acids; also keto-analogs of all of the above listed amino acids; partial hydrolysates of proteins and oligo and poly-peptides of synthetic origin; also phospholipids without limitation. As an option, antioxidants, preferably a tocopherol, may be included in formulations of this invention which deliver nutrients.

To prepare freeze dry compositions of food, the following preferred process is used (1) freeze a unit of the food composition, e.g., whole milk and liquified ammonia to −80° C. or below until the unit is converted into a frozen solid. (2) Next, deammoniate the frozen milk in a suitable container which permits the temperature to slowly rise to −20° C., and under vacuum conditions, the ammonia and water from the milk will sublime from the frozen state to the gas state in a matter of a few minutes. (3) Vacuum dry the product of step (2) at ambient temperature until no odor of ammonia remains. Completion of step (3) produces a finished powder product of freeze dried milk, a dry foodstuff. The product has the flavor of the natural product but has improved stability.

EXAMPLES

EXAMPLE 1

Mix the following ingredients together:
1 gram of flavored gelatin powder,
2 grams of maltodextrin,
0.5 gram of gelatin A,
2 grams of sucrose,
1 gram of aspartaine, and
70 mgs of powdered loperamide.

After mixing these components add the mixture to a container of about 100 mls of anhydrous liquified ammonia maintained at a temperature of about −40° C. Shake gently for approximately 30 minutes. A clear solution results. Prepare a mold to make the porous tablets by first rinsing the mold with a 10% solution of lecithin in 190 proof grain alcohol and then drying the mold at ambient temperature. Fill each compartment in the mold with 3 mls. of the solution described immediately above. Next, store the mold with its product at a temperature of about −80° C. or lower for about 30 minutes or until the molded tablets are frozen. Next, remove the frozen tablets from the mold and place in a suitable container, such as the chamber of a lyophilizer, which is permitted to slowly come to ambient temperature and pressure. The ammonia rapidly escapes from the frozen tablets into the gas state. Next, vacuum the tablets until no odor of ammonia remains. On completion of this step, the composition comprises a finished product.

EXAMPLE 2

Example 2 follows the procedure of Example 1 except that 0.5 grams of powdered erythromycin is used in place of loperamide.

EXAMPLE 3

Example 3 follows the procedure of Example 1 except that aspartaine is not used and the pouring temperature of the product into the mold is −30° C. instead of −40° C.

EXAMPLE 4

The method of Example 1 is followed except that two drops of cherry flavoring is added by pipette to the surface of each frozen tablet before placing the tablets in the chamber of the lyophilizer.

EXAMPLE 5

The method of Example 1 is followed except that the finished tablets are processed by a granulator to produce a granular porous solid dosage form.

EXAMPLE 6

The ingredients of Example 1 are used except that a 10% solution of ammonia in water is used in place of the anhydrous liquid ammonia. The mixture is stirred at a temperature of about 0° C. until a clear solution results. Fill the compartments as in the method of Example 1. Store the mold at about −20° C. until the tablets are frozen solid. Next, remove the tablets and place in the chamber of a lyophilizer. Lyophilize until no odor of ammonia remains and the tablets are dry.

EXAMPLE 7

The method of Example 6 is followed except that a 5% solution of ammonia is used in place of the 10% solution of ammonia.

It will be understood that the present disclosure has been made only by way of a number of preferred embodiments and that numerous changes in details of construction, combination and arrangement of parts can be resorted to without departing from the spirit and scope of the invention as herein claimed.

What is claimed is:

1. A method of manufacturing a porous carrier material having sufficient rigidity for carrying and administration of an active material selected from the group consisting of drugs, nutrients, vitamins, biologically-active compounds, foodstuffs, and combinations thereof comprising the steps of:
   (a) freezing a liquified ammonia solution comprising liquid ammonia, a liquid ammonia-soluble gel or foam material and a rigidifying agent for said gel or foam material, wherein the rigidifying agent is selected from the group consisting of a monosaccharide, a polysaccharide, and combinations thereof; and
   (b) deammoniating the frozen material from step (a) by causing material transfer of ammonia from the frozen state to the gas state.

2. The method of claim 1 further including adding a flavoring material to the surface of the porous carrier material, after ammonia removal.

3. The method of claim 1 further including the step of adding the active material to the ammonia solution prior to freezing said ammonia solution.

4. The method of claim 1 further including the step of adding the active material to the carrier material after the carrier material is deammoniated.

5. The method of claim 1, wherein step (b) is performed under vacuum conditions.

6. The method of claim 1, wherein the gel or foam material is a proteinaceous material selected from the group consisting of gelatin, gelatin A, gelatin B, fluid gelatin, modified fluid gelatin, albumin, and lecithin.

7. The method of claim 1, wherein the rigidifying material is selected from the group consisting of dextrose, fructose, galactose, mannitol, xylitol, sorbitol, sucrose, lactose, maltose, dextrans, dextran derivatives and combinations thereof.

8. The method of claim 1, wherein the rigidifying agent is maltodextrin.

9. The method of claim 1, wherein the maltodextrin has a weight average molecular weight of about 40,000 to about 90,000.

10. The method of claim 1, wherein the liquified ammonia is anhydrous liquid ammonia.

11. The method of claim 1, wherein the liquid ammonia comprises an aqueous solution of liquid ammonia containing ammonia in an amount of about 10% ammonia to about 99% ammonia.

12. The method of claim 11, wherein the saccharide is frozen with the aqueous ammonia solution at a temperature of about 0° C. to about −80° C.

* * * * *

UNITED STATES PATENT AND TRADEMARK OFFICE
CERTIFICATE OF CORRECTION

PATENT NO. : 5,382,437
DATED : JANUARY 17, 1995
INVENTOR : BERNARD ECANOW

It is certified that error appears in the above-identified patent and that said Letters Patent is hereby corrected as shown below:

Column 1, line 47, delete "inventions" and substitute therefor -- invention, --; and Column 1, line 66, after "gel" insert -- or --.

Signed and Sealed this

Eighteenth Day of April, 1995

*Attest:*

BRUCE LEHMAN

*Attesting Officer*

Commissioner of Patents and Trademarks